(12) United States Patent
Swift et al.

(10) Patent No.: US 10,702,406 B2
(45) Date of Patent: Jul. 7, 2020

(54) PROSTHESIS WITH FLEXIBLE STENT (71) Applicant: COOK MEDICAL TECHNOLOGIES LLC, Bloomington, IN (US)

(72) Inventors: Richard A. Swift, South Bend, IN (US); Keith R. Milner, West Lafayette, IN (US); James C. Merk, Terre Haute, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 38 days.

(21) Appl. No.: 15/936,753

(22) Filed: Mar. 27, 2018

(65) Prior Publication Data
US 2018/0280168 A1 Oct. 4, 2018

Related U.S. Application Data

(60) Provisional application No. 62/478,300, filed on Mar. 29, 2017.

(51) Int. Cl.
*A61F 2/90* (2013.01)
*A61F 2/915* (2013.01)
(Continued)

(52) U.S. Cl.
CPC .................. *A61F 2/90* (2013.01); *A61F 2/07* (2013.01); *A61F 2/852* (2013.01); *A61F 2/915* (2013.01);
(Continued)

(58) Field of Classification Search
None
See application file for complete search history.

(56) References Cited

U.S. PATENT DOCUMENTS 5,776,183 A 7/1998 Kanesaka et al.
5,964,798 A 10/1999 Imran
(Continued)

FOREIGN PATENT DOCUMENTS

WO   WO 2007/051183   5/2007

OTHER PUBLICATIONS

Extended European Search Report for 18275042.2 dated Jun. 12, 2018, 8 pgs.
(Continued)

*Primary Examiner* — Brian A Dukert
*Assistant Examiner* — Rebecca Lynee Zimmerman
(74) *Attorney, Agent, or Firm* — Brinks Gilson & Lione (57) ABSTRACT

A prosthesis is disclosed including an expandable frame having a first region and a second region coupled to one another. The first region includes a transition segment and a flex segment. The stent members of the transition segment have proximal and distal apices arranged in a peak-to-peak relationship with one another. At least a portion of proximal and distal apices of the transition segment remains uncoupled to one another. The flex segment includes a stent member having proximal and distal apices arranged in a peak-to-valley relationship with the transition segment. Longitudinal tie bars are intermittently coupled between apices the flex segment and the transition segment at coupling joints. The coupling joint is located where the proximal and distal apices of the stent members of the transition segment remain uncoupled to one another. The transition and flex segments may form an alternating pattern. A flareable proximal portion may be included.

17 Claims, 6 Drawing Sheets

(51) Int. Cl.
  *A61F 2/07*   (2013.01)
  *A61F 2/852*  (2013.01)
  *A61F 2/82*   (2013.01)
  *A61F 2/06*   (2013.01)

(52) U.S. Cl.
  CPC ... *A61F 2002/061* (2013.01); *A61F 2002/821* (2013.01); *A61F 2002/91541* (2013.01); *A61F 2002/91558* (2013.01); *A61F 2250/0018* (2013.01); *A61F 2250/0048* (2013.01)

(56) References Cited

U.S. PATENT DOCUMENTS

| | | | |
|---|---|---|---|
| 6,019,789 | A | 2/2000 | Dinh et al. |
| 6,206,916 | B1 | 3/2001 | Furst |
| 6,436,104 | B2 | 8/2002 | Hojeibane |
| 6,464,720 | B2 | 10/2002 | Boatman et al. |
| 6,602,282 | B1 | 8/2003 | Yan |
| 6,673,102 | B1 | 1/2004 | Vonesh et al. |
| 6,846,323 | B2 | 1/2005 | Yip et al. |
| 7,867,272 | B2 | 1/2011 | Niermann |
| 2002/0120327 | A1 | 8/2002 | Cox et al. |
| 2007/0191926 | A1* | 8/2007 | Nikanorov ............ A61F 2/91 623/1.15 |
| 2007/0293940 | A1 | 12/2007 | Schaeffer et al. |
| 2013/0325141 | A1* | 12/2013 | Gill ............ A61F 2/90 623/23.7 |
| 2014/0025157 | A1* | 1/2014 | Abunassar ............ A61F 2/915 623/1.15 |
| 2014/0155986 | A1 | 6/2014 | Ainsworth et al. |
| 2014/0207227 | A1 | 7/2014 | McGhie |
| 2015/0119972 | A1 | 4/2015 | Davis |

OTHER PUBLICATIONS

Notice of Intention to Grant European Patent 18275042.2 dated Feb. 19, 2020, 46 pgs.

\* cited by examiner

PROSTHESIS WITH FLEXIBLE STENT

PRIORITY CLAIM

This invention claims the benefit of priority of U.S. Provisional Application Ser. No. 62/478,300, entitled "Prosthesis with Flexible Stent," filed Mar. 29, 2017, the disclosure of which is hereby incorporated by reference in its entirety.

BACKGROUND

This disclosure relates to medical devices, and more particularly, to endoluminal devices and methods for making and using such endoluminal devices.

The functional vessels of human and animal bodies, such as blood vessels and ducts, occasionally weaken or even rupture. For example, an aortic wall can weaken, resulting in an aneurysm. Upon further exposure to hemodynamic forces, such an aneurysm can rupture, resulting in internal bleeding.

Various interventions have been provided for weakened, aneurysmal, dissected or ruptured vessels, including surgical interventions and endovascular interventions. Endovascular interventions generally include inserting an endoluminal device or prosthesis such as a stent or stent graft into the damaged or diseased body lumen to provide support for the lumen, and to exclude damaged portions thereof. The endovascular prosthesis is delivered in a radially compressed configuration using a catheter delivery system. The catheter is introduced into the lumen system remotely of the repair site and the prosthesis is delivered to the repair site intraluminally. The prosthesis is then radially expanded to engage the luminal wall. The prosthesis may provide some or all of the functionality of the original, healthy vessel and may further preserve any remaining vascular integrity.

Often times, a body lumen may be damaged in an area that includes a branch vessel. For example, there are at least three branch vessels extending from the abdominal aorta, each leading to various body organs. These branch vessels include the celiac, mesenteric, and renal arteries. When an aneurysm includes or is adjacent to one or more of these branch vessels, the prosthesis system must be able to exclude the aneurysm while maintaining fluid flow through the branch body lumen. Various stent grafts have been provided for repairing main body lumens and spanning branch vessels without occluding fluid flow thereto. For example, a main body stent graft may be provided that has one or more fenestrations or apertures in the sidewall of the stent graft. The stent graft can be deployed so that the fenestration is aligned with a branch vessel.

In many cases, particularly where the damaged portion is positioned at the junction between the main body lumen and the branch body lumen, or where the ostium of the branch vessel is damaged, a main stent graft is insufficient to adequately repair the luminal system. In these situations, it may be preferable to provide a branch lumen prosthesis for positioning within the branch vessel. The branch lumen prosthesis may be used independently, or in conjunction with a main body prosthesis.

A branch vessel prosthesis should be capable of complying with a variety of challenging and often competing demands. For example, the branch vessel prosthesis should preferably be highly flexible and capable of tracking through and conforming to a highly tortuous luminal environment. If the prosthesis includes a balloon-expandable stent, the stent should be sufficiently resilient so as not to hinder balloon expansion and/or molding. On the other hand, once the prosthesis is implanted in the body lumen, it must be sufficiently strong and robust to survive a highly dynamic and pulsatile luminal environment that can promote prosthesis damage. This is of particular concern where the branch vessel prosthesis is deployed within a fenestration of a main body prosthesis. During the cardiac cycle, the main body prosthesis will pulse and move with the main body vessel, placing stress on the branch vessel prosthesis at the fenestration. When the main body prosthesis moves, it can exert significant concentrated and localized stresses on the branch vessel prosthesis through the fenestration. Over time, this cyclic wear can cause the branch vessel prosthesis to weaken and eventually to crush under the force of the main body prosthesis, requiring further medical intervention.

SUMMARY

Examples of prostheses are described herein. In one example, the prosthesis includes an expandable tubular frame having a lumen longitudinally extending therein about a longitudinal axis. The frame includes a longitudinal first region coupled to a longitudinal second region, wherein the longitudinal second region is proximal to and has a greater radial stiffness than the longitudinal first region. The longitudinal first region includes a first annular segment and an annular flex segment adjacent to one another. The first annular segment includes a proximal first annular stent member and a distal first annular stent member adjacent to one another. Each of the proximal and distal first annular stent members includes proximal and distal apices arranged in a peak-to-peak relationship with one another. At least a portion of the distal apices and corresponding proximal apices of the respective proximal and distal first annular stent members remain uncoupled to one another. The annular flex segment includes at least one second annular stent member having proximal and distal apices arranged in a peak-to-valley relationship with the proximal and distal first annular stent members. A longitudinal tie bar is coupled between one of the proximal apices of the second annular stent member and one of the proximal apices of the distal first annular stent member at a coupling joint. The coupling joint is located where the distal and the corresponding proximal apices of the proximal and distal first annular stent members remain uncoupled to one another.

In another example, a prosthesis includes an expandable tubular frame having a lumen longitudinally extending therein about a longitudinal axis. The frame includes a longitudinal first region coupled to a longitudinal second region, wherein the longitudinal second region is proximal to the longitudinal first region. The longitudinal first region includes a transition segment and a flex segment adjacent to one another. The transition segment includes a pair of annular stent members adjacent to one another. Each of the annular stent members of the transition segment includes proximal and distal apices arranged in a peak-to-peak relationship with one another and coupled to one another intermittently such that a portion remains uncoupled to one another to define a plurality of dual-diamond shaped cells circumferentially disposed from one another. The flex segment includes an annular stent member having proximal and distal apices arranged in a peak-to-valley relationship with the annular stent members of the transition segment. A plurality of longitudinal tie bars is intermittently coupled between the proximal apices of the annular stent member of the flex segment and the proximal apices of the annular stent member of the transition segment at a plurality of coupling joints. Each of the coupling joints is located where the proximal and distal apices of the pair of annular stent members of the transition segment remain uncoupled to one another.

In another example, a prosthesis includes a balloon expandable tubular frame having a lumen longitudinally extending therein about a longitudinal axis. The frame includes a longitudinal first region coupled to a longitudinal second region, wherein the longitudinal second region is proximal to the longitudinal first region. The longitudinal first region includes an alternating pattern of a transition segment and a flex segment adjacent to one another. Each transition segment includes a plurality of annular stent members adjacent to one another. Each of the annular stent members of the transition segment includes proximal and distal apices arranged in a peak-to-peak relationship with one another and coupled to one another intermittently such that a portion of the proximal and distal apices remains uncoupled to one another. Each flex segment includes an annular stent member having proximal and distal apices arranged in a peak-to-valley relationship with the annular stent members of each transition segment. A plurality of longitudinal tie bars is intermittently coupled between the proximal apices of the annular stent member of each flex segment and the proximal apices of the proximalmost annular stent member of each transition segment at a plurality of coupling joints. Each of the coupling joints is located where the proximal and distal apices of the pair of annular stent members of each transition segment remain uncoupled to one another. A plurality of second longitudinal tie bars is coupled between the distal apices of the annular stent member of each flex segment and the distal apices of one of the distalmost annular stent members of each transition segment at a plurality of distal coupling joints. Each of the distal coupling joints is located where the proximal and distal apices of the annular stent members of each transition segment remain uncoupled to one another.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE INVENTION

Medical devices for implantation within a human or animal body for repair of damaged vessels, ducts, or other physiological pathways are provided. The medical devices may include a prosthesis with a stent for support. On the balance, the stent design may provide high radial force, suitable bending flexibility, and greater fatigue endurance for a variety of treatment applications. The stent design may also offer greater stability during crimping, which is an improvement for a stent cut from a full-sized cannula. When the prosthesis is a branch prosthesis coupled within a fenestrated prosthesis, the stent design may contribute to the positioning accuracy relative to the fenestration and suitable securement to the fenestration ring. The stent may be covered with graft material or uncovered, that is, a bare metal stent, depending on the application.

Throughout the specification, when referring to a prosthesis, or a structure or component of a prosthesis, the terms "distal" and "distally" denote a position, direction, or orientation that is generally downstream in the direction of fluid flow relative to the heart. Accordingly, the terms "proximal" and "proximally" denote a position, direction, or orientation that is generally upstream in the direction of fluid flow relative to the heart.

Figure 1:
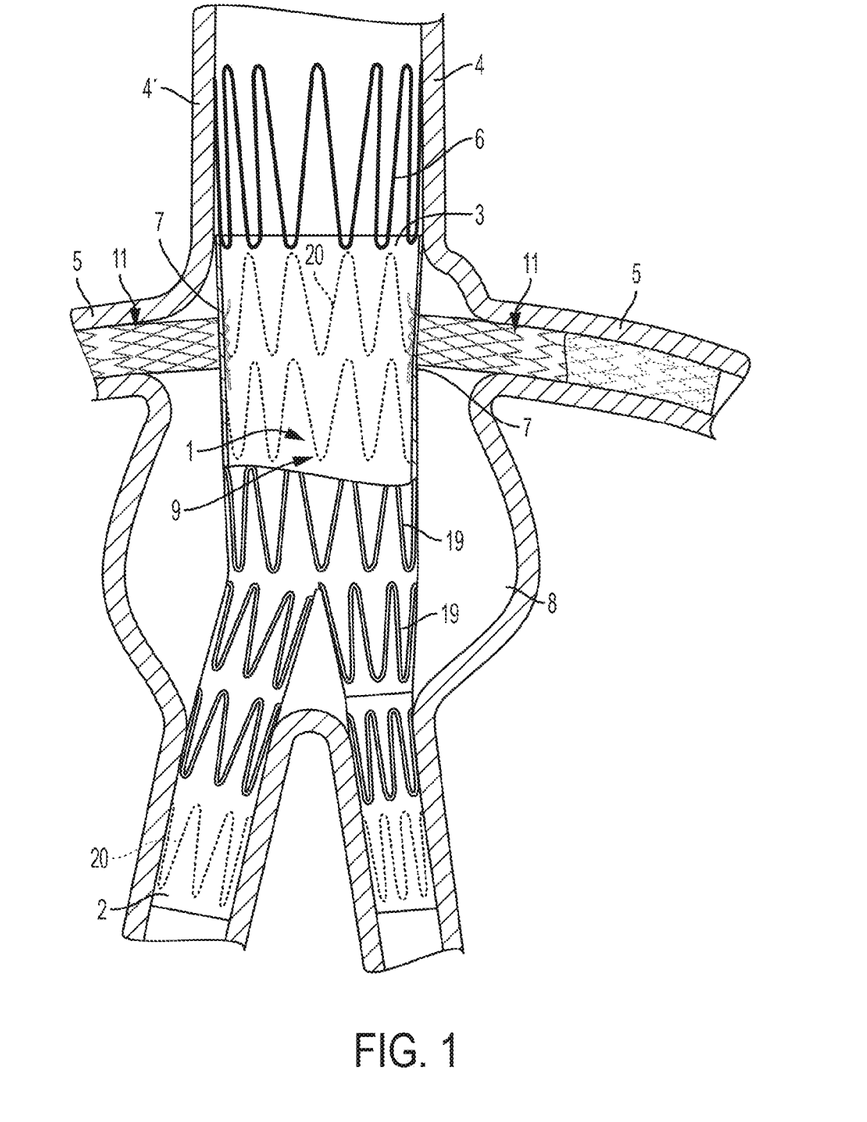
FIG. 1 depicts a schematic view of deployment of the side branch prosthesis from a main vessel prosthesis.

FIG. 1 shows a schematic view of the deployment of a main vessel prosthesis 1 into a main body vessel, such as an aneurysed aorta 4, and the deployment of side branch vessel prostheses 11 from the main vessel prosthesis 1 into side branch vessels 5, such as, for example, renal arteries. Although the branching vessels shown are the renal arteries, other branching vessels from the aorta may also benefit from such arrangement, including, for example, the superior mesenteric artery (SMA), celiac artery, iliac arteries, innominate/brachiocephalic artery, left carotid artery and left subclavian artery. To this end, the main vessel prosthesis and the side branch vessel prosthesis may be substantially orthogonal as shown or may be obliquely arranged depending on the relative angle between the artery and the aorta, or other branching vessel and main vessel.

The main vessel prosthesis 1 includes a distal end 2 and a proximal end 3 and is shown deployed into the aneurysed region 8. The main vessel prosthesis 1 may have a suprarenal uncovered stent 6, which is received in a non-aneurysed region 4' of the aorta upstream of the aneurysm and provides a top support for the main vessel prosthesis 1. The main aneurysed region 8, however, extends distally past the side branch vessels 5 and as such is necessary to provide side branch vessel prostheses to these vessels. The main vessel prosthesis 1 includes two fenestrations 7 or holes that are configured to align with the side branch vessels 5. The abdominal aorta 4 and the side branch vessels 5 form a branched body lumen system.

It will be noted that the side branch vessel prostheses 11 extending from the main vessel prosthesis 1 to the side branch vessels 5 may cross a region of aneurysed region 8. If there was movement of the main vessel prosthesis 1 with respect to the aneurysm and if there was a non-rigid portion of the side branch vessel prosthesis 11 in this space the lumen of the side branch vessel prosthesis 11 may be closed off by kinking. This rigid portion of the side branch vessel prostheses 11 in this region may act to prevent this kinking event from occurring.

The main vessel prosthesis 1 preferably includes a graft material 9, such as, for example, one of the disclosed graft materials below. The main vessel prosthesis 1 may further include one or more stents 19, 20. The stents 19, 20 may be positioned internally and/or externally of the graft material 9. In one example, the prosthesis 1 may comprise the internal stent 20 at one or both ends 2, 3. The internal stent 20 provides a smooth external prosthesis surface to help seal the respective ends of the main vessel prosthesis 1 against an adjoining vascular wall or against an interconnecting module. Stents 19, 20 may include any suitable stent configuration known in the art. The stents 19, 20 may be balloon-expandable or self-expanding. For example, stents 19, 20 may comprise self-expanding Z stents. The prosthesis may comprise a combination of stents 19, 20 or a single stent having both balloon-expandable and self-expanding properties. The internal stents 20 may comprise radially disposed barbs (not shown) that extend through the graft material to engage the surrounding vessel wall, thereby anchoring the prosthesis 1 to the vessel and preventing migration of the main vessel prosthesis 1 once it is deployed.

Figure 2:
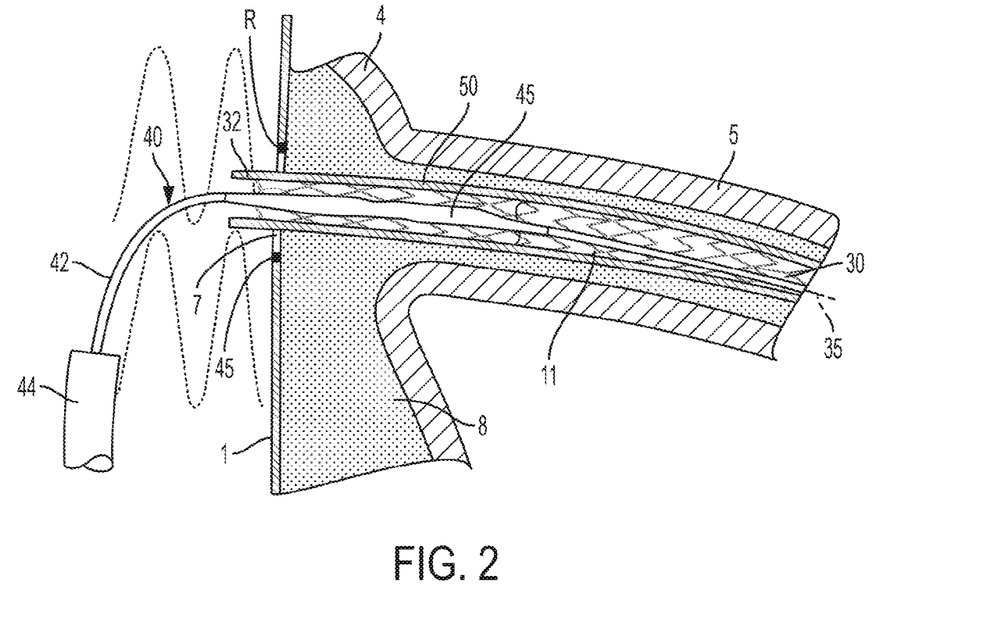
FIGS. 2-5 show various stages of deployment of the side branch prosthesis into a branch vessel from a main vessel prosthesis.

As can be seen in FIG. 2, the main vessel prosthesis 1 has been deployed into the aorta 4 and extends through the aneurysed region 8. The main vessel prosthesis 1 the fenestration 7 with radiopaque markers R around its periphery which assist a surgeon in locating the fenestration 7 with respect to the side branch vessel 5, shown as the renal artery, after the main vessel prosthesis 1 has been deployed. The main vessel prosthesis 1 may provide a fluid seal against the aorta 4 at positions proximal and distal of the aneurysed region 8, thereby excluding blood flow from the damaged area. Fenestrations 7 are provided so that blood flow is maintained to the side branch arteries 5. Main vessel prosthesis 1 is configured to repair the aneurysm 8.

Once the main vessel prosthesis 1 has been deployed, the branch prosthesis delivery device can be inserted via a surgical cut-down into an artery, or by percutaneous access techniques that are well known in the art. A distal end 30 of the side branch vessel prosthesis 11 extends distally into the branch vessel 5 and a proximal end 32 of the prosthesis 11 extends proximally through the fenestration 7 into the main vessel prosthesis 1. A guide wire 35 is deployed within the side branch vessel 5. A deployment device 40 includes the crimped and loaded prosthesis 11, and is introduced and moved over the guide wire 35 to position the side branch vessel prosthesis 11 at the treatment site as shown in FIG. 2. The deployment device 40 includes a guide wire catheter 42 with a nose cone (not shown) at one end and an outer sheath 44 for covering and holding the prosthesis 11 in a radially compressed or collapsed condition. On the guide wire catheter 42 is an inflatable balloon 45, which can be inflated with suitable material to expand the prosthesis 11 as required. It is contemplated that in some embodiments the balloon can be provided on a separate balloon catheter deployed over the guide wire 35 after the deployment of the device.

The outer sheath 44 is shown withdrawn from the crimped side branch vessel prosthesis 11. The side branch vessel prosthesis 11 may include a graft material, such as any one of the graft materials described below. The branch vessel prosthesis 11 includes a stent frame structure 50. The branch vessel prosthesis 11 is configured to seal against the side branch vessel 5. The fenestration 7 forms a seal between the branch vessel prosthesis 11 and the main vessel prosthesis 1 and assists in anchoring the branch vessel prosthesis 11 in the vasculature. The balloon 45, however, has not been expanded and therefore the frame 50 of the side branch vessel prosthesis 11 is not fully radially expanded.

Figure 3:
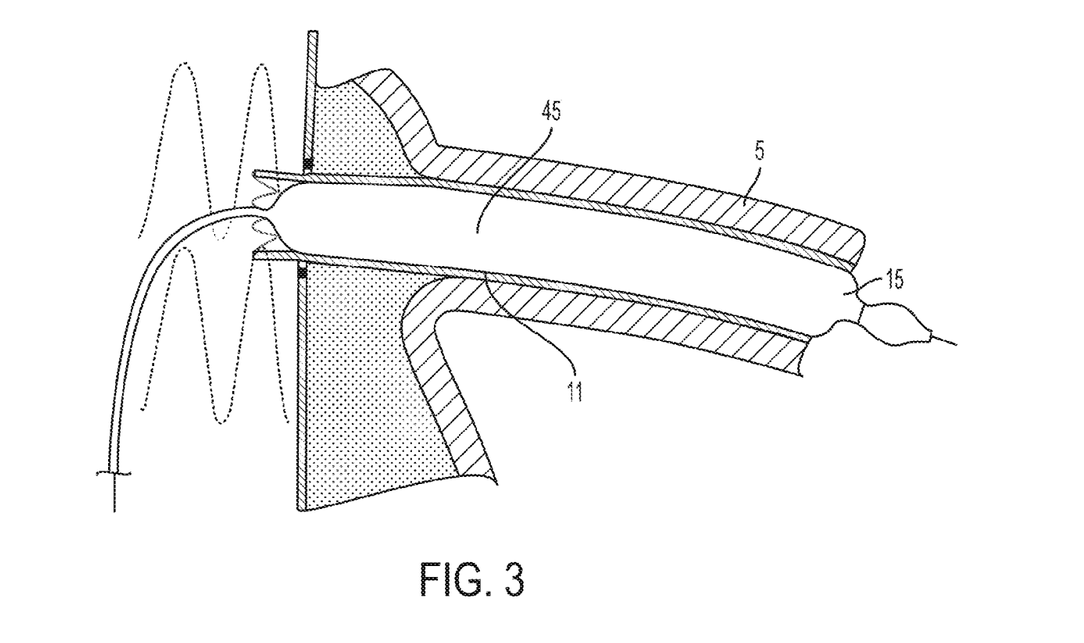

As can be seen in FIG. 3, the balloon 45 has been radially expanded by known means and the frame 50 has expanded to engage against the walls of the side branch vessel 5. The balloon 45 is then deflated and the deployment device 40 on the guide wire 35 is then removed leaving the guide wire 35 in place.

Figure 4:
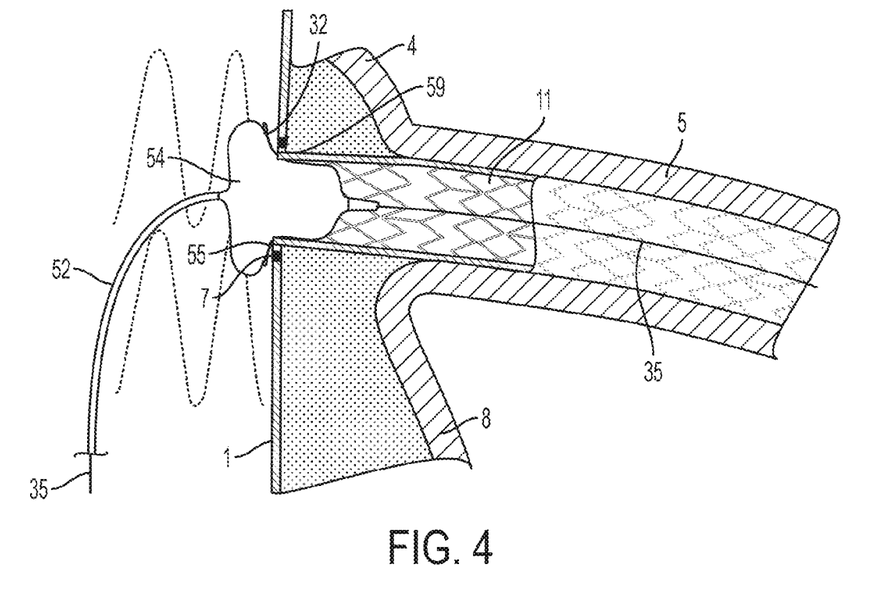

As depicted in FIG. 4, another balloon catheter 52 is then deployed over the guide wire 35. The balloon 54 on the balloon catheter 52 is positioned so that the balloon 54 is partially within the proximal end 32 of the side branch vessel prosthesis 11 and partially outside the side branch vessel prosthesis 11 in the region of the fenestration 7 for being expanded. Expansion causes the flareable portion 55 of the frame 50 to be flared so that the proximal end 32 of the side branch vessel prosthesis 11 has a larger cross-sectional area than the fenestration 7 and is firmly received within the fenestration 7 of the main vessel prosthesis 1. The balloon catheter 82 may comprise any balloon configuration suitable for expanding the prosthesis 11 and for flaring the flareable portion 36. For example, the balloon may comprise a first balloon portion for expanding the frame 50 and the coupling portion, and a second balloon portion for further expanding the flareable portion 55. U.S. Pat. No. 8,287,586 to Schaeffer et al. and U.S. Pat. No. 9,095,461 to Schaeffer, and U.S. Patent Application Publication No. 2005/0149166 to Schaeffer et al., disclose delivery systems for endoluminal prostheses having single and multiple balloons, of which the delivery system subject matter is incorporated herein by reference. The delivery systems disclosed therein may be used with the present disclosed prosthesis.

Figure 5:
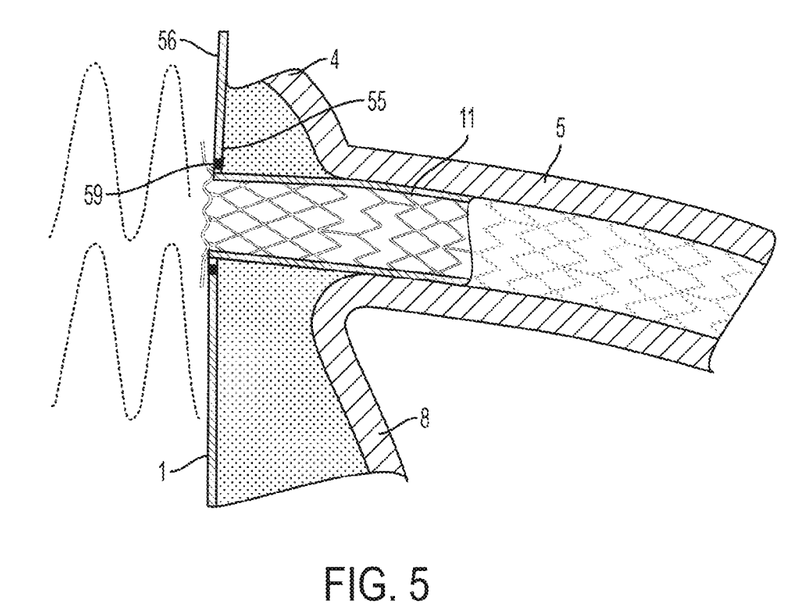

As shown in FIG. 5, the flaring can be extended to the extent that the flareable portion 55 is completely flared against the inside wall 56 of the main vessel prosthesis 1. As shown in FIGS. 4-5, the branch vessel prosthesis 11 is deployed within the branch vessel and through the fenestration 7. The fenestration is shown having a reinforcing member 59. The reinforcing member 59 may at least partially surround a perimeter of the fenestration 7. The reinforcing member 59 is configured to engage the branch prosthesis 11 and provide improved support and sealing between the main vessel prosthesis 1 and the branch vessel prosthesis 11. The reinforcing member 59 may comprise a metal ring or gasket, such as for example, stainless steel or nitinol. The reinforcing member 59 may be associated with the radiopaque markers R.

A blood flow path is therefore provided from the main vessel prosthesis 1 into the branch vessel 5, which includes a rigid portion across the aneurysed space 8 and a more flexible portion within the branch vessel 5. This will assist with prevention of stenosis at the junction between the prosthesis and the side branch vessel.

Figure 6:
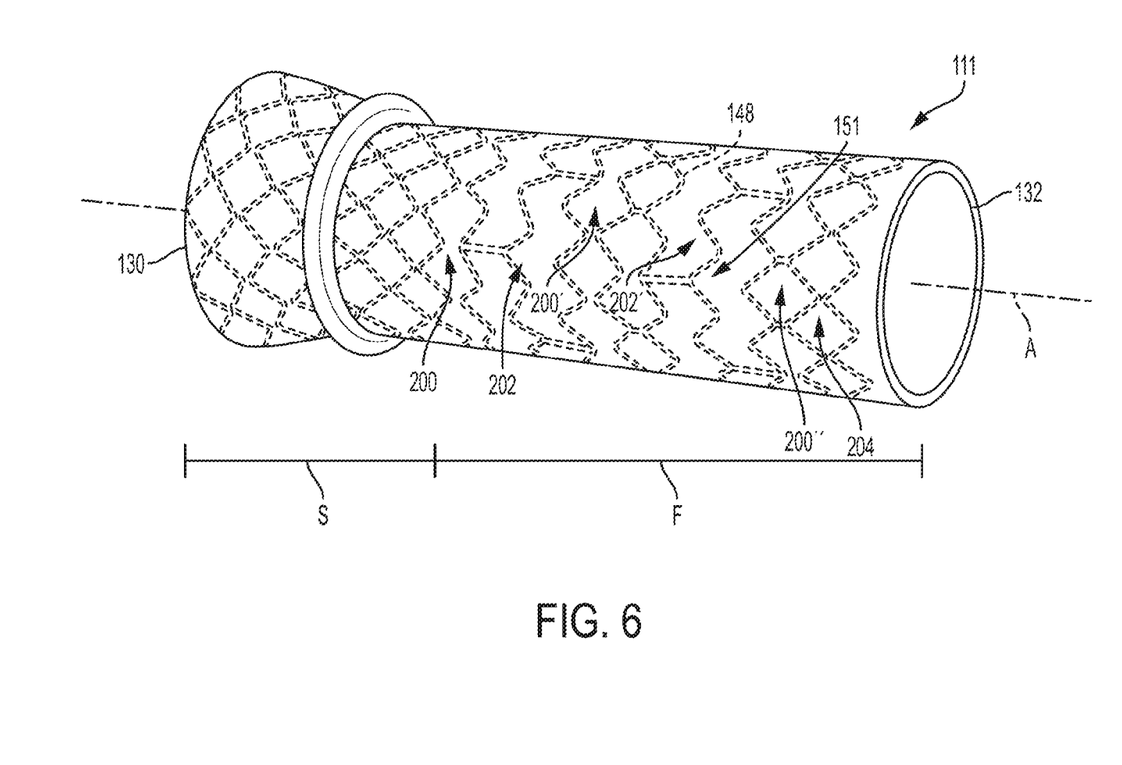
FIG. 6 is a perspective view of an example of an expanded side branch prosthesis.

FIG. 6 illustrates one example of the branch prosthesis (now referred to as 111) in a radially expanded configuration. The elongated prosthesis 111 includes an expandable tubular stent frame 148 extending about a longitudinal axis A. With additional reference to FIG. 7, the frame 148 is shown rolled out in a plane. The frame 148 extends between a proximal end 130 and a distal end 132. The frame 148 comprises a longitudinal first region F coupled to a longitudinal second region S that is disposed more proximal than the first region F. The first region F has greater longitudinal bending flexibility than the second region S, as shown more clearly in FIG. 11. The second region S has greater radial strength than the first region F.

Figure 7:
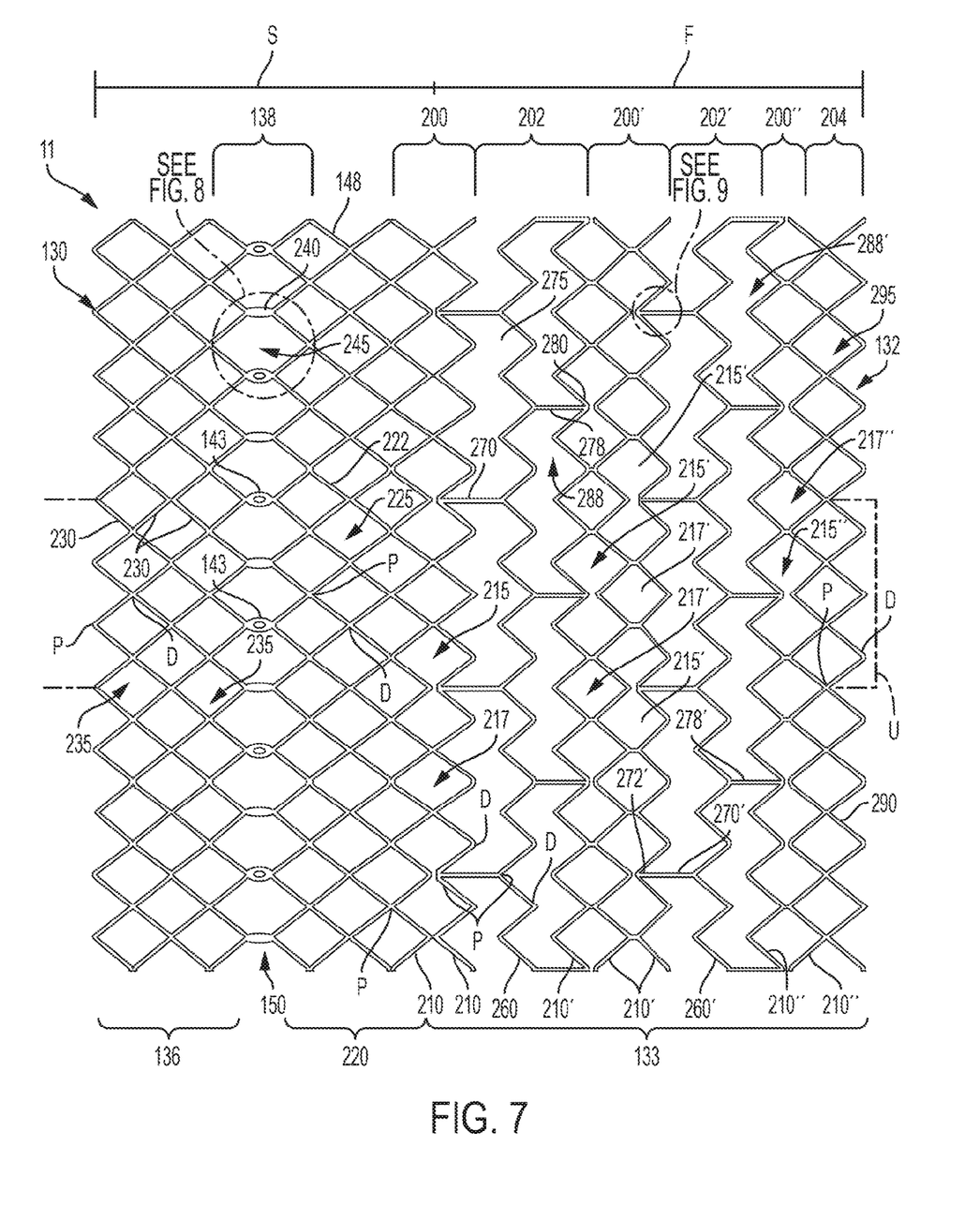
FIG. 7 is a planar view of an example of a rolled out stent frame for a prosthesis.

In FIG. 7, the first region F includes a generally tubular body portion 133, and the second region S includes a flareable proximal end portion 136. The body portion 133 and the flareable portion 136 are radially disposed about the longitudinal axis A. The body portion 133 is configured to extend distally into the branch lumen. The flareable portion 136 is configured to extend proximally into the fenestration 7 of main vessel prosthesis 1. The flareable portion 136 extends proximally through the fenestration 7 of the main vessel prosthesis 1 and flares radially outwardly into the lumen of the main vessel prosthesis 1. In one example, at least a portion of the flareable portion 136 has a diameter that is greater than the diameter of the fenestration 7. The second region S includes a bending portion 150 is disposed between the flareable portion 136 and the body portion 133. The bending portion 150 is configured to bend to allow the flareable portion 136 to flare.

The second region S of the prosthesis 111 may include a coupling portion 138. The coupling portion 138 is disposed between the flareable portion 136 and the body portion 133. The body portion 133 is generally longer than the coupling portion 138. For example, the body portion 133 may be five to seven times longer than the coupling portion 138. The coupling portion 138 is configured to engage the fenestration 7 of the main vessel prosthesis 1 when the branch vessel prosthesis 111 is deployed. When deployed, the coupling portion 138 is in mechanical communication with the main vessel prosthesis 1.

The branch vessel prosthesis 111 may include a suitable biocompatible graft material 151, such as one of the graft materials described below. In another example, the graft material 151 is omitted from the branch vessel prosthesis 111. The frame may be fastened to the inner, the outer, or both surfaces of the graft. The graft material may cover the entire prosthesis or it may cover only a portion of the prosthesis. The frame may be balloon-expandable and/or self-expanding. Imageable markers 143, such as radiopaque markers, may be attached to or integral with the prosthesis 111. For example, an imageable marker 143 may be provided and configured to indicate the bending portion 150 or the coupling portion 138. The imageable marker 143 comprises a substance that is imageable in the body using, for example fluoroscopic techniques. For example, the marker may comprise gold.

Figure 11:
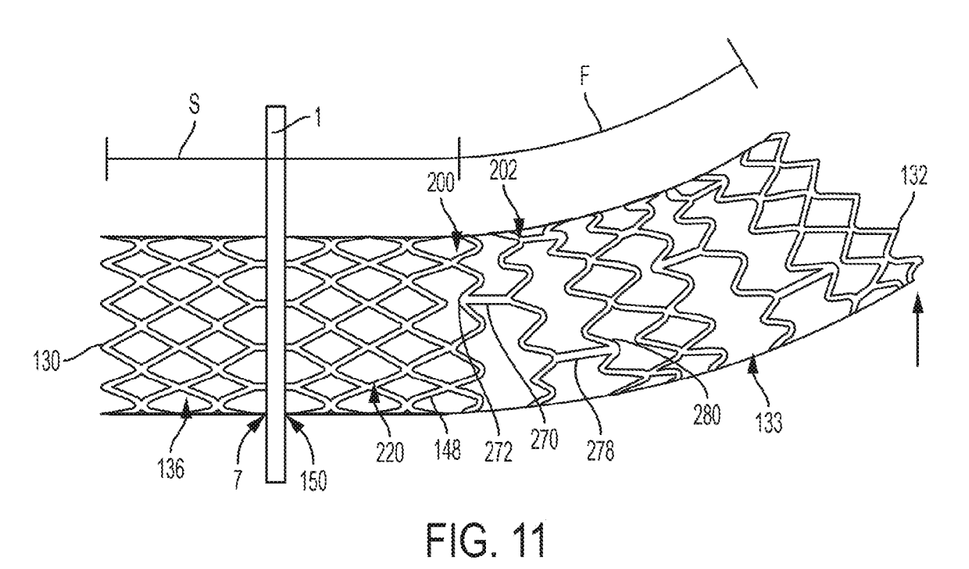
FIG. 11 is a side view an expanded side branch prosthesis under a bending load, depicting the relative position of the side branch prosthesis and a main vessel prosthesis.

The body portion 133 of the first region F may possess a high degree of longitudinally bending flexibility and resiliency, as shown in FIG. 11. During delivery, the prosthesis 111 may be capable of tracking tortuous body lumina. Additionally, the prosthesis 111 must be sufficiently resilient to allow for ease of balloon expansion. In use, the body portion 133 of prosthesis 111 is exposed primarily to radial compression due to luminal contraction and expansion. The body portion 133 is not exposed to significant crushing or bending loads. Accordingly, the body portion 133 does not require a high degree of crush-resistance.

The terms "crush-resistant" and "crush-resistance" are used throughout the specification and in the appended claims. It is noted that these terms are intended to refer to the measure of the ability of a structure to withstand plastic deformation when the structure is exposed to a concentrated and localized stress. The crush-resistance of a stent may be estimated experimentally by determining the yield strength, or the minimum force required to plastically deform the stent. Crush-resistance may be a function of material selection, as well as stent structure and design.

The flareable portion 136 may possess a high degree of conformability. To deploy the branch vessel prosthesis 111, the flareable portion 136 is expanded and flared to a greater diameter into the ostium of the branch vessel or into the lumen of the main vessel prosthesis 1. This may be accomplished by using an expandable balloon, as shown in FIGS. 4-5, to plastically deform or "iron" the flareable portion 136 from a tubular configuration into a flared configuration. If the flareable portion 136 is flexible, it will be relatively easy to flare. Conversely, if the flareable portion 136 is too rigid, it may be difficult to deploy. The flareable portion 136 does not require a high degree of crush-resistance because once the prosthesis 111 is deployed, the flareable portion 36 does not receive significant loading.

The coupling portion 138, on the other hand, preferably comprises a high degree of crush-resistance. In use, the cardiac cycle may cause the main vessel prosthesis 1 to pulse and to move along its axis. The distal end 132 of the branch vessel prosthesis 111 may be anchored within the branch lumen, such as, for example, with barbs or anchor elements, and the proximal end 130 of the prosthesis 111 is anchored by the main vessel prosthesis 1 within the fenestration 7. As the main vessel prosthesis 1 pulses, the edges defining the fenestration 7 of the prosthesis 1 may exert a concentrated stress on the coupling portion 138. This concentrated stress is particularly great where the fenestration 7 comprises the reinforcing member 59 described above. The stress causes the prosthesis 111 to bend, resulting in tensile, compression, and shear strain in the region of the coupling portion 138 adjacent and in contacting engagement with the fenestration 7. Over time, this pulsatile stress can cause the coupling portion 138 to plastically deform and to crush under the weight of the main vessel prosthesis 1.

It is important to note that crush-resistance, as used herein, is not synonymous with radial strength. The radial strength of an expanded prosthesis is a measure of its ability to withstand elastic deformation when exposed to a uniform distributed radial stress. As noted above, the crush-resistance of an expanded prosthesis, on the other hand, is a measure of its ability to withstand plastic deformation when exposed to a concentrated and localized stress that includes bending. A prosthesis may comprise significant radial strength but have poor crush-resistance. Conversely, a prosthesis may comprise very low radial strength but have high crush-resistance.

In one example, the body portion 133 is coupled to the flareable portion 136 via the bending portion 150 and the coupling portion 138. The bending portion 150 is configured to bend to allow the flareable portion 136 to flare radially outwardly during deployment. The body portion 133, the coupling portion 138, the bending portion 150, and the flareable portion 136 are radially disposed about the longitudinal axis A.

The body portion 133 of the first region F includes at least a first annular segment 200 and a second annular flex segment 202 adjacent to the first annular segment. An end annular segment 204 may be coupled along the distal end 132 of the frame. The first annular segment 200 includes a pair of adjacent proximal and distal first annular stent members 210. Each of the first annular stent members 210 includes interconnected struts having proximal apices P and distal apices D in an endless undulating pattern arranged in a peak-to-peak relationship. As used herein, the terms "peak" and "valley" are used interchangeably to refer to bends or apices in portions of a frame. The term "peak-to-peak" used herein refers to the circumferential alignment of proximal apices of annular stent member with distal apices of an adjacent stent member. The term "peak-to-valley" used herein refers to the circumferential alignment of proximal apices of annular stent member with proximal apices of an adjacent stent member, and may also referred to when the proximal apices of annular stent member are circumferentially offset from the distal apices of an adjacent stent member.

At least a portion of proximal apices P of the distal first annular stent member 210 and the corresponding distal apices D of the proximal first annular stent member 210 in a peak-to-peak relationship remain uncoupled to one another. In one example, there is a coupled pair of proximal apices P and distal apices D, and the circumferentially adjacent pair of the proximal apices P and distal apices D may remain uncoupled to define an open cell, such as, for example, a dual-diamond shaped cell 215. The intermittent coupling of the apices provide the dual-diamond shaped cells. In another example, there is an alternating pattern of a coupled pair of proximal and distal apices, the adjacent pair of the proximal and distal apices in the first circumferential direction remaining uncoupled to define a dual-diamond shaped cell 215, and the adjacent pair of the proximal and distal apices in the opposite second circumferential direction coupled to define a closed cell, such as, for example, a diamond shaped cell 217. To this end, the pair of the first annular stent members are arranged and intermittently coupled at their apices to define an alternating pattern including single diamond shaped cells 217 and dual-diamond shaped cells 215.

The second region S may include a second region tubular body portion 220 coupling the coupling portion 138 to the first region's proximal most first annular stent member 210. In one example, the second region tubular body portion 220 may be omitted such that the proximal most first annular stent member 210 is coupled to the coupling portion 138. In the example shown, the second region tubular body portion 220 includes three longitudinally interconnected body annular stent members 222. It is contemplated that the second region tubular body portion 220 may vary to include one or more longitudinally interconnected body annular stent members 222 and may depend on the size of the extension for anchoring into the healthy tissue of the branch vessel. The stent members 222 include annular second region stent members including interconnected struts having proximal and distal apices in an endless undulating pattern arranged in a peak-to-peak relationship. The stent members 222 are shown having the proximal and distal apices coupled to one another to form closed cells, such as, for example, single diamond shaped cells 225. In one example, the stent members 222 are arranged to define a plurality of closed single diamond shaped cells circumferentially disposed relative to one another. The first annular stent members 210 are oriented to maintain the peak-to-peak relationship with the second region stent members 222.

The coupling portion 138, the bending portion 150, and the flareable portion 136 of the second region S may also include includes a plurality of longitudinally interconnected annular stent members 230. It is contemplated that the number of stent members forming the flareable body portion 136 may vary, depending on the radial expansion diameter and flaring diameter needed for anchoring with the fenestration. The stent members 230 include interconnected struts having proximal apices and distal apices in an endless undulating pattern arranged in a peak-to-peak relationship. The stent members 230 are shown with the proximal and distal apices coupled to one another to form closed cells, such as, for example, closed single diamond shaped cells 235. The stent members 230 are oriented to maintain the peak-to-peak relationship with the second region stent members 222. The plurality of proximal apices P and distal apices D coupled to one another provides structural support and radial stiffness to these portions 136, 150, 220. In one example, all of the proximal and distal apices are coupled to one another in at least one of these portions, and all of the portions as shown in FIG. 7.

In one example, the flareable portion 136 is coupled to the second region tubular body portion 220 through the bending portion 150. The bending portion 150 is configured to minimize the stress imposed by the flareable portion 236 on the second region tubular body portion 220 and the tubular portion 133 in the expanded configuration by providing a region of relative flexibility. Increasing the flexibility of bending portion 150 increases the ability of the flareable portion 136 to flare-out in the expanded configuration. Flaring of the flareable portion 136 is thus facilitated by the bending portion 150.

Figure 8:
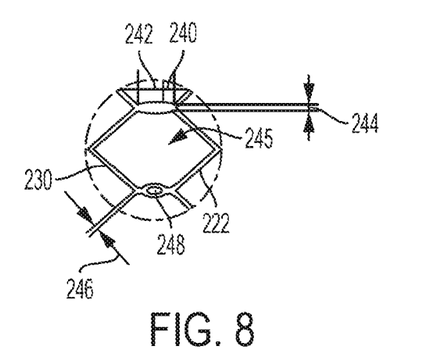
FIG. 8 is a detailed view of a bending portion of the stent frame depicted in FIG. 7.

With additional reference to FIG. 8, the bending portion 150 may comprise at least two bendable connector elements 240 that connect the flareable portion 136 to the second region tubular body portion 220. The number of connector elements 240, and therefore the frequency of the points of attachment between the flareable portion 136 and the second region tubular body portion 220 may be varied to facilitate bending in the bending portion 150. The connector elements 240 have a length 242 to further increase the relative distance between the annular stent members 230 and stent members 222 and form closed cells 245 having a cross-sectional area larger than the diamond shape cells 225 and/or 235.

The connector elements 240 may be further configured for enhanced bending. In one example, the length 242 may be selected from the range between about 0.85 mm to about 1.05 mm, and in some examples, between 0.8 to 1.0 mm, and in one example, the length is 0.9 mm whereas the length between coupled proximal and distal apices in the other portions in the second region is minimal. The length between coupled proximal and distal apices in the transition segments 200 may be also be minimal, and in some examples, the length is selected from the range between about 0.2 mm to about 0.4 mm, and in some examples, between 0.25 to 0.35 mm, and in one example, the length is 0.3 mm. The width 244 of connector elements 240 may also be wider than the width 246 of the struts in the flareable portion 136 to the second region tubular body portion 220. In one example, the width 244 is about twice the width as the width 246. In one example, the width 244 is about 0.16 mm to about 0.26 mm, and in one embodiment, the width is 0.21 mm. In one example, the width 246 is about 0.06 mm to about 0.16 mm, and in one embodiment, the width is 0.11 mm. The wider width 244 of the connector element 240 gives the element a lesser thickness/width ratio compared to the struts with widths 246, which may make it more conducive to bending for a strut height or thickness of about 0.17 mm to about 0.22 mm. The thickness/width ratio of the connector element 240 is selected in a range of 0.5 to 0.55 times the thickness/width ratio of the struts with width 246. In one example, the connector element 240 has a thickness/width ratio of 0.83 (0.175 mm/0.21 mm), while the struts with width 246 has a thickness/width ratio of 1.59 (0.175 mm/0.11 mm). Connector elements 240 may be disposed between every pair of proximal apices and distal apices, as shown.

Connector elements 240 may be non-linear or arcuate in shape or may be generally linear, as illustrated in FIG. 8. Connector elements 240 may, for example, comprise a "V" shape, an "S" shape, or a "W" shape. Where the prosthesis 11 comprises a graft material, for example a coating or film of plastic (such as PTFE), the bending portion 150 may include the graft. For example, the flareable portion 136 and the combination of the second region tubular body portion 220 and the body portion 233 may comprise separate stent structures that are longitudinally displaced from each other and are connected through the graft. At least a portion of the connector elements 240 may include an aperture 248 formed radially therein. The aperture 248 may be sized and shaped to receive the imageable markers 143, which may be bonded, mechanically fixed, and/or otherwise securely fixed within the aperture 248. The stent may include a plurality of markers 143 disposed radially about the prosthesis that generally indicate the coupling portion 138. Each of the imageable markers 143 may have the shape of an eyelet.

The coupling portion 138 is disposed intermediate the second region tubular body portion 220 and the flareable portion 136. The coupling portion 138 includes at least one of the stent members 230 and the stent members 222 in closest proximity to the connector element 240 and thus the bending portion 150. In FIG. 7, the coupling portion 138 of the stent includes a pair of coupling stent members: one disposed proximally of the bending portion 150, and the other disposed distally of the bending portion 150. The coupling portion 138 is configured to be more crush-resistant than the second region tubular body portion 220, the body portion 133 and the flareable portion 236.

The second annular flex segment 202 includes at least one second annular stent member 260 including interconnected struts having proximal apices P and distal apices D in an endless undulating pattern arranged in a peak-to-valley relationship with the distalmost first annular stent member 210 that is longitudinally the closest to the second annular stent member 260.

Figure 9:
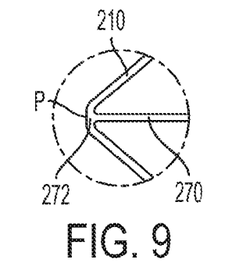
FIG. 9 is a detailed view of a coupling joint of the stent frame depicted in FIG. 7.
Figure 10:
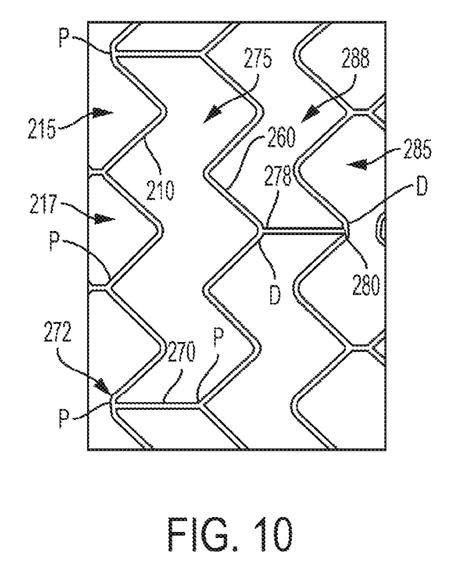
FIG. 10 is a detailed view of a partial flex segment of the stent frame depicted in FIG. 7.

The second annular flex segment 202 includes a longitudinal tie bar 270 coupled between a proximal apex P of the second annular stent member 260 and a proximal apex P of the distalmost first annular stent member 210 at a coupling joint 272, as shown in FIGS. 9-10. The coupling joint 272 is located where the proximal apices P and distal apices D of the proximal and distal first annular stent members 210 remain uncoupled to one another. The geometric characteristics of this joint 272 or 280 may provide suitable transition in radial stiffness and flexibility from the first annular segment 200 to the second annular flex segment 202. The transitional first annular segment 200 may provide higher radial stiffness than the second annular flex segment 202 but lesser radial stiffness than the second region tubular body portion 220. The second annular flex segment 202 may provide higher bending flexibility than each of the first annular segment 200 and the second region tubular body portion 220, as shown in FIG. 11. The first annular segment 200 may have a radial stiffness that is about 2.0 to 2.4 times, and in one example, 2.2 times, the radial stiffness of the second annular flex segment 202. The second region tubular body portion 220 may have a radial stiffness that is 1.0 to 1.2 times, and in one example, 1.1 times the radial stiffness of the first annular segment. The second region tubular body portion 220 may have a radial stiffness that is 2.2 to 2.6 times, and in one example, 2.4 times, the radial stiffness of the second annular flex segment 202. The second annular flex segment 202 may have a bending flexibility that is 3.5 to 4.5 times, and in one example, 4 times, more flexible than the bending flexibility of the first annular segment 200. The first annular segment 200 may have a bending flexibility that is 10 to 18 times, and in one example, 14 times, more flexible than the bending flexibility of the second region tubular body portion 220. The second annular flex segment 202 may have a bending flexibility that is 45 to 55 times, and in one example, 50 times, more flexible than the bending flexibility of the second region tubular body portion 220. In one example, the longitudinal tie bars 270 are coupled between a proximal apex P of the second annular stent member 260 and the proximal apex P that splits the dual-diamond shaped cell 215. In one example, a plurality of longitudinal tie bars 270 are coupled along the annular region at each split of the dual-diamond shaped cells 215. The shapes of the open cells 275 of the second annular flex segment 202 is not a diamond shaped. Rather, the shape of the cells 275 is a multi-W shape as shown in the figures. The cross-sectional area of the individual cells 275 in the second annular flex segment 202 is larger than the individual cells 215 of the first annular segment 200.

Enhanced flexibility of the body portion 133 along the annular segments 200, 202 may be provided in many ways. For example, the shape of longitudinal tie bars 270 may be varied to affect the flexibility of the body portion 133. The longitudinal tie bars 270 may comprise an "I" shape (as shown), a "V" shape, an "S" shape, a "W" shape, or any other arcuate or undulating shape. The number and configuration of the longitudinal tie bars 270 can also be varied to affect the flexibility of the body portion 133. For example, increasing the frequency of longitudinal tie bars 270 results in generally lower flexibility, while decreasing the frequency of longitudinal tie bars 270 results in generally higher flexibility. Further, the body portion 133 may be made more flexible by decreasing the thickness of any of the longitudinal tie bars.

FIG. 11 also depicts the relative positioning of each of the portions and segments of the frame 148 relative to the fenestration 7 of the main vessel prosthesis 1. The bending portion 150 with the imageable markers is shown aligned with the wall of the fenestration. The flareable portion 136, prior to the flaring step, is shown extending proximally within the main vessel prosthesis. The second region tubular body portion 220 maintains a cylindrical profile by extending distally away from the main vessel prosthesis by a predetermined distance, about 3 mm to about 8 mm. The first region F is shown longitudinally bending distally beyond the second region tubular body portion 220. The bending configuration also illustrates the varied flexing of the transition segment 200 and flex segment 202 from the second region tubular body portion 220 to the distal end 132. For example, the flex segments 202 allow the distance between adjacent stent members to be relatively closer under a compression load (as shown along the upper side of the prosthesis) and relatively farther apart under tensile load (as shown along the lower side of the prosthesis).

The frame 148 may include alternating patterns of first annular segments 200 and second annular flex segments 202, as shown in FIG. 7. In one example, the frame 148 includes a second of the first annular segments (referred to as 200') disposed distal to the second annular flex segment 202. In another example, the frame includes a second of the second flex segments (referred to as 202') disposed distal to the second of the first annular segments 200'. In another example, the frame 148 includes a third of the first annular segments (referred to as 200'') disposed distal to the second annular flex segment 202. The alternating patterns of the first segment and the second flex segment may continue to provide additional length to the frame. Disposed at the distal end 132 of the frame 148 and interconnected with the distalmost of the first annular segments (shown as segment 200") is the end annular segment 204, as will be described below.

The second of the first annular segments 200' includes one or more of the design features as described in relation to the first annular segments 200. To this end, the second annular flex segment 202 may include a second longitudinal tie bar 278 coupled between a distal apex D of the second annular stent member 260 and a distal apex D of the proximalmost first annular stent member (now referred to as 210') of the second of the first annular segments 200' at a distal coupling joint 280 where the proximal apices P and the corresponding distal apices D of the stent members 210' remain uncoupled to one another.

In one example, the second longitudinal tie bars 278 are coupled between a distal apex D of the second annular stent member 260 and the distal apex D that splits the dual-diamond shaped cell 215' of the second of the first annular segments 200'. In one example, a plurality of second longitudinal tie bars 278 are coupled along the annular region at each split of the dual-diamond shaped cells 215' of the second of the first annular segment 200'. The shapes of the open cells 288 of the second annular flex segment 202 is not a diamond shaped. Rather, the shape of the cells 288 a multi-W shape. The shape of the cell 288 may be a mirror image of the shape of the cell 275. The cross-sectional area of the individual cells 288 in the second annular flex segment 202 is larger than the individual cells 215 of the first annular segment 200.

The relative circumferential position of the longitudinal tie bars 270 and the second longitudinal tie bars 278 may vary. In one example, the circumferential spacing between the longitudinal tie bars 270, 278 are equal. In one example, the longitudinal tie bars are circumferentially offset from the second tie bars 278 at equal distances.

The second of the first annular segments 200' may include a pair of the first annular stent members 210' arranged to define an alternating annular pattern of single diamond shaped cells 217' and dual-diamond shaped cells 215'. In another example, the second of the first annular segments 200' include a third first annular stent member 210' arranged to define a second alternating annular pattern of single diamond shaped cells 217' and dual-diamond shaped cells 215' that is adjacent and distal to the first pattern. The third first annular stent member 210' is disposed at the distalmost position of the three. The second pattern and the first pattern may be offset from one another such that the single diamond shaped cell 217' of the first pattern is disposed along a center of the dual-diamond shaped cells 215' in the second pattern. The stent members 210' are oriented to maintain the peak-to-peak relationship with each other and with the stent members 210 of the first annular segments 200, and the peak-to-valley relationship with the stent member 260 of the second annular flex segment 202.

In another example, the frame 148 includes a second of the second flex segments (referred to as 202'). The second of the second flex segments 202' may have one or more of the design features in the description of the second flex segments 202. The second of the second flex segments 202' includes the stent member (now referred to as 260') oriented to maintain the peak-to-valley relationship with the stent members 210' of the second of the first annular segments 200' and the peak-to-peak alignment with the stent member 260 of the second annular flex segment 202. For example, the second of the second flex segments 202' includes the longitudinal tie bar (now referred to as 270') coupling the stent member 260' with the adjacent stent member 210'. In one example, the longitudinal tie bar 270' is coupled between a proximal apex P of the second annular stent member 260' and a proximal apex P of the distalmost first annular stent member 210' at the coupling joint (now referred to as 272').

In one example, a plurality of longitudinal tie bars 270' are coupled along the annular region at each split of the dual-diamond shaped cells 215'. The shapes of the open cells 275' of the second annular flex segment 202' is not a diamond shaped. Rather, the shape of the cells 275' is a multi-W shape. The cross-sectional area of the individual cells 275' in the second annular flex segment 202' is larger than the individual cells 215, 215' of the first annular segments.

In another example, the frame 148 includes a third of the first annular stent members (referred to as 202"). The third of the first annular segments 200" includes one or more of the design features as described in relation to the first annular segments 200. The third of the first annular segments 200" may include a pair of the first annular stent members (now referred to as 210") arranged to define an alternating annular pattern of single diamond shaped cells (now referred to as 217") and dual-diamond shaped cells (now referred to as 215"). The stent members 210" are oriented to maintain the peak-to-peak relationship with each other and with the stent members 210 of the first annular segments 200 and the peak-to-valley relationship with the stent member 260' of the second of the second annular flex segment 202'.

The second annular flex segment 202' may include the second longitudinal tie bar (now referred to as 278') coupled between a distal apex D of the second annular stent member 260' and a distal apex D of the proximalmost first annular stent members 210" of the third of the first annular segments 200" at the coupling joint (now referred to as 280') where the proximal apices P and distal apices D of the stent members 210" remain uncoupled to one another. In one example, the second longitudinal tie bars 278' are coupled between a distal apex D of the second annular stent member 260' and the distal apex D that splits the dual-diamond shaped cell 215" of the third of the first annular segments 200". In one example, a plurality of second longitudinal tie bars 278' are coupled along the annular region at each split of the dual-diamond shaped cells 215" of the third of the first annular segment 200". The shapes of the open cells (now referred to as 288') of the second annular flex segment 202' is not a diamond shaped. Rather, the shape of the cells 288' a multi-W shape. The shape of the cell 288' may be a mirror-image of the shape of the cell 275'. The cross-sectional area of the individual cells 288' in the second annular flex segment 202' is larger than the individual cells 215, 215', 215" of the first annular segments.

The end annular segment 204 of the frame 148 includes an end stent member 290 including interconnected struts having proximal apices P and distal apices D in an endless undulating pattern arranged in a peak-to-peak relationship relative to the distalmost stent member of the first segment, shown as stent members 210" of the third of the first annular segments 200". The coupling between the stent members 290 and 210" are shown having the proximal and distal apices coupled to one another to form closed cells, such as, for example, single diamond shaped cells 295. In one example, the stent members 290, 210" are arranged to define a plurality of closed single diamond shaped cells circumferentially disposed relative to one another. The end annular segment 204 is configured to have a radial stiffness that is greater than the radial stiffness of the first annular segments 200, 200', 200" and the second annular flex segments 202, 202'.

The number of annular couplings between the apices in the first annular segments 200, 200', 200" may be about twice the number coupling in the second annular flex segment 202, 202' via the longitudinal tie bars. The longitudinal tie bars and the coupled pairs of apices provide structural support and elasticity to the body portion. For example, the interconnection frequency between adjacent stent members in the flareable portion 136, the bending portion 150, the region tubular body portion 220, and the end annular segment 204 may be generally greater than the interconnection frequency between adjacent stent members in any of the first annular segments 200, 200', 200" and/or any of the second annular flex segments 202, 202'. As used herein, "interconnection frequency" refers to the number of points of attachment between adjacent cells per unit.

In FIG. 7, the interconnection frequency along the frame 148 varies along the longitudinal direction. For example, the interconnection frequency is at its relatively lowest along the second annular flex segments 202, 202', such as, for example, one connection per unit U. The interconnection frequency is at its relatively highest along the flareable portion 136, the bending portion 150, the second region tubular body portion 220, and the end annular segment 204', such as, for example, four connections per unit U. The interconnection frequency is intermediate between its relative lowest and highest along the first annular segments 200, 200', 200", such as, for example, two connections per unit U. Because the interconnection frequency along the second annular flex segments is relatively low, these flex segments will tend to be more flexible than the remaining segments. On the other hand, because the interconnection frequency along the flareable portion 136, the bending portion 150, second region tubular body portion 220, and the end annular segment 204' is relatively high, these regions will tend to be more radially stiffer than the remaining segments, and be better equipped to receive and disperse contact loading from the fenestration 7, and will be generally more crush-resistant. In addition to the interconnection frequency, the plurality of closed cells along these regions as shown may also contribute to more uniform radial expansion upon deployment.

Because the interconnection frequency along the first annular segments 200, 200', 200" is relatively intermediate, these segments dispersed between the second flex segments will tend to have greater radial stiffness than the second flex segments. To this end, the first annular segments 200, 200', 200" provide the relatively flexible first region F of the frame 148 with improved stability during crimping and radial compression. The first annular segments 200, 200', 200" may also provide the frame improved fatigue performance and loading characteristics as these transition segments 200, 200', 200" provide transitional radial stiffness segments from the radially stiffer second region S and the radially stiffer end segment 204 to the relatively higher flexible second flex segments. This improvement in part may be contributed to the interconnection frequency, but also, may be contributed to the interconnection pattern to define a combination of alternating closed cells and open cells along the circumference, which may also contribute to improved circumferential compression. Another part of the contribution in improvement may be the coupling joint configuration where the longitudinal tie bars are coupled to apices of stent members that remain uncoupled from adjacent apices. These coupling joints provide flexible connections between the segments, which may lower the bending stiffness. One or more of the advantages of the frame with the disclosed arrangement and design is a stent frame with high radial force and high resistance to circumferential compression, along with suitable bending flexibility.

The term "graft" describes an object, device, or structure that is joined or that is capable of being joined to a body part to enhance, repair, or replace a portion or a function of that body part. Grafts that can be used to repair body vessels include, for example, films, coatings, or sheets of material that are formed or adapted to conform to the body vessel that is being enhanced, repaired, or replaced. The graft material may include a biocompatible synthetic or biomaterial. Examples of suitable synthetic materials include fabrics, woven and nonwoven materials, and porous and nonporous sheet materials. Other synthetic graft materials include biocompatible materials such as polyester, polytetrafluoroethylene ("PTFE"), polyurethane ("PU"), fluorinated ethylene propylene ("FEP") and the like. Examples of suitable biocompatible materials include, for example, pericardial tissue and extracellular matrix materials ("ECMM") such as SIS.

Other synthetic materials, such as biocompatible synthetic materials, may be used for the graft material. Synthetic materials may include polymers such as, for example, poly (urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly (methacrylic acid), polylactides ("PLA"), polyglycolides ("PGA"), poly(lactide-co-glycolid-es) ("PLGA"), polyanhydrides, polyorthoesters or any other similar synthetic polymers that may be developed that are biocompatible. Biocompatible synthetic polymers also may include copolymers, blends, or any other combinations of the forgoing materials either together or with other polymers generally. The use of these polymers will depend on given applications and specifications required. Suitable polymer material may include, for example, polyester such as DACRON™, polyetherurethanes such as THORALON® from Thoratec Corporation (Pleasanton, Calif.), or polyethylene terephthalate ("PET").

In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any polymer that may be formed into a porous sheet can be used to make a graft material, provided the final porous material is biocompatible. Polymers that can be formed into a porous sheet include polyolefins, polyacrylonitrile, nylons, polyaramids and polysulfones, in addition to polyesters, fluorinated polymers, polysiloxanes and polyurethanes as listed above. The porous sheet may be made of one or more polymers that do not require treatment or modification to be biocompatible.

The graft material, the coating, or one class of materials for electrospinning may also include extracellular matrix materials. The "extracellular matrix" is typically a collagen-rich substance that is found in between cells in animal tissue and serves as a structural element in tissues. Such an extracellular matrix is preferably a complex mixture of polysaccharides and proteins secreted by cells. The extracellular matrix can be isolated and treated in a variety of ways. Following isolation and treatment, it is referred to as an "extracellular matrix material," or ECMM. ECMMs may be isolated from submucosa (including small intestine submucosa), stomach submucosa, urinary bladder submucosa, tissue mucosa, renal capsule, dura mater, liver basement membrane, pericardium or other tissues.

In addition to xenogenic biomaterials, such as SIS, autologous tissue can be harvested as well. Additionally Elastin or Elastin Like Polypetides (ELPs) and the like offer potential as a material to fabricate the covering or frame to form a device with exceptional biocompatibility. Another alternative would be to use allographs such as harvested native valve tissue. Such tissue is commercially available in a cryopreserved state. In addition, a bare metal stent or a covered stent could be coated with an anti-restenotic agent, such as paclitaxel, sirilomis or other equivalent. In addition, the graft can be coated with an anti-thrombogenic agent, such as heparin.

The stent or support frame 148 may be any device or structure that provides or is configured to provide rigidity, expansion force, or support to a body part, for example, a diseased, damaged, or otherwise compromised body lumen. Such stent frame structure may include any suitable biocompatible material, including, but not limited to fabrics, metals, plastics, and the like. Examples of suitable materials include metals such as stainless steel and shape memory materials, such as nitinol, and plastics such as PET, PTFE and polyurethane. The stent frame structure may be "expandable," that is, it may be capable of being expanded to a larger-dimension configuration. The stent frame structure may expand by virtue of its own resilience (i.e., self-expanding), upon the application of an external force (i.e., balloon-expandable), or by a combination of both. The stent struts that are interconnected to one another represents specific configurations of a wire member that comprises a basic structural component of the stent. As used herein, the term "strut" refers to any filamentary member, including, but not limited to, drawn wire and filaments that have been laser cut from a cannula. For example, the stent architecture with the intricate interconnecting elements and patterns may lend itself to being manufacture from a metal cannula laser cut to the desired pattern as described. The shape, size, and dimensions of the stent structure may vary. The size of these components and the overall stent structure is determined primarily by the diameter of the vessel lumen at the intended implant site, as well as the desired length of the overall stent device. The stent structure and/or ring structures may have a common cross-sectional area along the body or may vary to have different cross-sectional areas.

In one example, the stent frame structure is entirely balloon-expandable. Balloon-expandable stent frames may be made of stainless steel, such as, 316LSS, CoCr or alloy thereof, such as CoCr L605 alloy, moly-rhenium alloys, or other metal material suitable for balloon expansion and exhibiting desired properties.

Where the stent frame is formed by laser cutting from a metal cannula or tube the diameter of the metal cannula may have a diameter of from 3 mm to 40 mm and have a wall thickness of from about 35 microns to about 0.5 mm. In one example, the cannula is sized nominally for 8 mm. In one example, a metal cannula or tube of L605 alloy is provided. The L605 cannula includes an as-cut outer diameter of 8.4 mm and a cannula wall thickness of 0.2 mm. In another example, a metal cannula or tube of 316 L alloy is provided. The 316 L cannula includes an as-cut outer diameter of 8.433 mm and a cannula wall thickness of 0.216 mm. For any cannula configuration, the strut and stent member pattern of the frame disclosed herein is laser cut from cannula in a well-known manner. As known, an electropolishing step may be applied to the cannula. As a result, the cannula wall thickness in the L605 may be reduced to 0.175 mm, while the 316 L cannula wall thickness may be reduced to 0.1905 mm. The cannula may be suitably heat treated to make it deformable and resilient. It is contemplated that other sized cannula may be used and further processed to result in a nominal diameter of an 8 mm inner diameter frame. For example, a nominal diameter of a 5 mm inner diameter cannula may be processed and machine to result in a nominally expanded inner diameter of 8 mm.

When the prosthesis includes a graft material, the graft material may be attached to the as-cut stent frame by various means. The graft material may be attached to the as-cut stent frame by stitching, for example by using a monofilament or braided suture material. The graft material also may be affixed to the as-cut stent frame by dipping the as-cut stent frame in a liquefied polymer and allowing the polymer to solidify into a film. The liquefied polymer may be a molten polymer or a polymer or pre-polymer before curing or cross-linking occurs. Layers of graft materials may be applied along the luminal surface and/or abluminal surface of the as-cut stent frame and heat and/or pressure may be applied to the construct such that the graft material layers bond to another and to the as-cut stent frame. The attached graft material to the as-cut stent frame at the intended diameter of the body may reduce the potential of weakening the graft material and tearing. As a result, thinner graft materials may be used which may reduce the profile of the prosthesis upon crimping. Attachment of the graft material to the as-cut stent frame at a reduced diameter requires expansion and heat treatment of the stent frame to the desired expanded diameter for treatment, subsequent compression in a crimped state for delivery and radial expansion for deployment.

To clarify the use of and to hereby provide notice to the public, the phrases "at least one of <A>, <B>, . . . and <N>" or "at least one of <A>, <B>, <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

What is claimed is:

1. A prosthesis extending about a longitudinal axis between a proximal end and a distal end, the prosthesis comprising:

an expandable tubular frame having a lumen longitudinally extending therein about a longitudinal axis, the frame including a longitudinal first region coupled to a longitudinal second region, wherein the longitudinal second region is proximal to and has a greater radial stiffness than the longitudinal first region, the longitudinal first region comprising a first annular segment and an annular flex segment adjacent to one another, the first annular segment including a proximal first annular stent member and a distal first annular stent member adjacent to one another, each of the proximal and distal first annular stent members having proximal and distal apices arranged in a peak-to-peak relationship with one another, wherein at least a portion of the distal apices and corresponding proximal apices of the respective proximal and distal first annular stent members remain uncoupled to one another, the annular flex segment including at least one second annular stent member having proximal and distal apices arranged in a peak-to-valley relationship with the proximal and distal first annular stent members, wherein a longitudinal tie bar is coupled between one of the proximal apices of the second annular stent member and one of the proximal apices of the distal first annular stent member at a coupling joint, wherein the coupling joint is located where the distal and the corresponding proximal apices of the proximal and distal first annular stent members remain uncoupled to one another, wherein the proximal and distal apices of the proximal and distal first annular stent members are coupled intermittently to define a plurality of dual-diamond shaped cells and a plurality of diamond shaped cells circumferentially disposed from one another.

2. The prosthesis of claim 1, wherein the proximal and distal apices of the proximal and distal first annular stent members are coupled intermittently to define a plurality of dual-diamond shaped cells circumferentially disposed from one another.

3. The prosthesis of claim 2, wherein the coupling joint is disposed splitting one of the dual-diamond shaped cells.

4. The prosthesis of claim 1, wherein the plurality of dual-diamond shaped cells and the plurality of diamond shaped cells circumferentially disposed from one another define an alternating pattern of one of the diamond shaped cells and one of the dual-diamond shaped cells.

5. The prosthesis of claim 4, wherein a plurality of longitudinal tie bars is intermittently coupled between the proximal apices of the second annular stent member and the proximal apices of the distal first annular stent member at a plurality of coupling joints, wherein each of the coupling joints is disposed splitting each of the dual-diamond shaped cells.

6. The prosthesis of claim 1, wherein the longitudinal first region comprises an end annular segment including an end annular stent member having proximal and distal apices arranged in a peak-to-peak relationship with one of the proximal and distal first annular stent members of the second first annular segment and coupled to one another to define a plurality of diamond shaped cells circumferentially disposed from one another.

7. The prosthesis of claim 1, wherein the longitudinal second region includes a bending portion and a flareable portion configured to expand to greater diameter along the bending portion.

8. The prosthesis of claim 7, wherein the longitudinal second region includes a second region tubular body portion coupling the bending portion to the proximal first annular stent member, the second region tubular body portion includes a plurality of second region annular stent members having proximal and distal apices arranged in a peak-to-peak relationship with one another and with the proximal first annular stent member to define a plurality of diamond shaped cells circumferentially disposed from one another.

9. The prosthesis of claim 1, wherein the expandable tubular frame is balloon-expandable.

10. The prosthesis of claim 1, further comprising a graft material attached to the expandable tubular frame.

11. A prosthesis extending about a longitudinal axis between a proximal end and a distal end, the prosthesis comprising:
an expandable tubular frame having a lumen longitudinally extending therein about a longitudinal axis, the frame including a longitudinal first region coupled to a longitudinal second region, wherein the longitudinal second region is proximal to the longitudinal first region,
the longitudinal first region comprising a transition segment and a flex segment adjacent to one another, the transition segment including a pair of annular stent members adjacent to one another, each of the annular stent members of the transition segment having proximal and distal apices arranged in a peak-to-peak relationship with one another and coupled to one another intermittently such that a portion of the proximal and distal apices of the transition segment remains uncoupled to one another to define a plurality of dual-diamond shaped cells circumferentially disposed from one another, such that the plurality of dual-diamond shaped cells and a plurality of diamond shaped cells are circumferentially disposed from one another,
the flex segment including an annular stent member having proximal and distal apices arranged in a peak-to-valley relationship with the annular stent members of the transition segment, wherein a plurality of longitudinal tie bars is are intermittently coupled between the proximal apices of the annular stent member of the flex segment and the proximal apices of the annular stent member of the transition segment at a plurality of coupling joints, wherein each of the coupling joints are located where the proximal and distal apices of the pair of annular stent members of the transition segment remain uncoupled to one another.

12. The prosthesis of claim 11, wherein the expandable tubular frame is balloon-expandable.

13. The prosthesis of claim 11, wherein the longitudinal second region includes a bending portion and a flareable portion configured to expand to greater diameter along the bending portion.

14. The prosthesis of claim 13, wherein the longitudinal second region includes a second region tubular body portion coupling the bending portion to one of the annular stent members of the transition segment, the second region tubular body portion includes a plurality of second region annular stent members having proximal and distal apices arranged in a peak-to-peak relationship with one another and with the annular stent members of the transition segment, wherein the proximal and distal apices of the plurality of second region annular stent members are coupled to one another to define a plurality of diamond shaped cells circumferentially disposed from one another.

15. A prosthesis extending about a longitudinal axis between a proximal end and a distal end, the prosthesis comprising:
a balloon expandable tubular frame having a lumen longitudinally extending therein about a longitudinal axis, the frame including a longitudinal first region coupled to a longitudinal second region, wherein the longitudinal second region is proximal to the longitudinal first region, the longitudinal first region comprising an alternating pattern of a transition segment and a flex segment adjacent to one another, each transition segment including a plurality of annular stent members adjacent to one another, each of the annular stent members of the transition segment having proximal and distal apices arranged in a peak-to-peak relationship with one another and coupled to one another intermittently such that a portion of the proximal and distal apices of the transition segment remains uncoupled to one another, each flex segment including an annular stent member having proximal and distal apices arranged in a peak-to-valley relationship with the annular stent members of each transition segment, wherein a plurality of longitudinal tie bars is intermittently coupled between the proximal apices of the annular stent member of each flex segment and the proximal apices of the proximalmost annular stent member of each transition segment at a plurality of coupling joints, wherein each of the coupling joints is located where the proximal and distal apices of the pair of annular stent members of each transition segment remain uncoupled to one another, wherein a plurality of second longitudinal tie bars is coupled between the distal apices of the annular stent member of each flex segment and the distal apices of one of the distalmost annular stent members of each transition segment at a plurality of distal coupling joints, wherein each of the distal coupling joints is located where the proximal and distal apices of the annular stent members of each transition segment remain uncoupled to one another.

16. The prosthesis of claim 15, wherein the longitudinal first region comprises an end annular segment including an end annular stent member having proximal and distal apices arranged in a peak-to-peak relationship with the distalmost annular stent member of the distalmost transition segment and coupled to one another to define a plurality of diamond shaped cells circumferentially disposed from one another.

17. The prosthesis of claim 16, wherein the longitudinal second region includes a bending portion and a flareable portion configured to expand to greater diameter along the bending portion, and a second region tubular body portion coupling the bending portion to the proximalmost annular stent member of the proximalmost transition segment, the second region tubular body portion including a plurality of second region annular stent members having proximal and distal apices arranged in a peak-to-peak relationship with one another and with said proximalmost annular stent member of the transition segment, wherein the proximal and distal apices of the plurality of second region annular stent members are coupled to one another to define a plurality of diamond shaped cells circumferentially disposed from one another.

* * * * *